(12) United States Patent
Wells et al.

(10) Patent No.: US 8,094,299 B2
(45) Date of Patent: Jan. 10, 2012

(54) TRANSDUCER MODULE

(75) Inventors: Mark A. Wells, Davie, FL (US); Carlos A. Perez, Miami, FL (US); Jose M. Cano, Miami, FL (US)

(73) Assignee: Beckman Coulter, Inc., Brea, CA (US)

( * ) Notice: Subject to any disclaimer, the term of this patent is extended or adjusted under 35 U.S.C. 154(b) by 478 days.

(21) Appl. No.: 12/178,817

(22) Filed: Jul. 24, 2008

(65) Prior Publication Data

US 2010/0020308 A1    Jan. 28, 2010

(51) Int. Cl.
*G01N 21/01* (2006.01)
(52) U.S. Cl. ..................................... 356/244
(58) Field of Classification Search ............... 356/39–42
See application file for complete search history.

(56) References Cited

U.S. PATENT DOCUMENTS

| | | |
|---|---|---|
| 4,559,717 A | 12/1985 | Scire et al. |
| 5,125,737 A | 6/1992 | Rodriguez et al. |
| 5,616,501 A | 4/1997 | Rodriguez et al. |
| 5,798,827 A | 8/1998 | Frank et al. |
| 5,872,687 A | 2/1999 | Arya et al. |
| 5,874,311 A | 2/1999 | Li et al. |
| 6,042,249 A | 3/2000 | Spangenberg |
| 6,228,652 B1 | 5/2001 | Rodriguez et al. |
| 6,232,125 B1 | 5/2001 | Deka et al. |
| 7,008,792 B2 | 3/2006 | Lopez et al. |
| 7,208,319 B2 | 4/2007 | Lopez et al. |
| 7,468,789 B2 * | 12/2008 | Czarnek ........................ 356/246 |
| 2006/0126080 A1 * | 6/2006 | Kusuzawa ..................... 356/635 |
| 2006/0203226 A1 | 9/2006 | Roche et al. |
| 2007/0188737 A1 | 8/2007 | Fritz |

OTHER PUBLICATIONS

Poster presentation at International Society for Analytical Cytology (ISAC)—Abbott Cell Dyn Sapphire (May 2008).
International Search Report for International Application No. PCT/US2009/03219, mailed Jul. 30, 2009, 4 pgs.
Written Opinion of the International Searching Authority for PCT/US2009/03219, mailed Jul. 30, 2009, 7 pgs.

* cited by examiner

*Primary Examiner* — Michael P Stafira
(74) *Attorney, Agent, or Firm* — K&L Gates LLP; Louis C. Cullman; Thomas A. Turano (57) ABSTRACT

Transducer modules for use in a blood analysis instrument and methods for analyzing a blood sample. The transducer modules presented generally include a light source, a focus-alignment system, a flow cell, and a light scatter detection system. Electrodes within the flow cell allow for the measurement of the DC impedance and RF conductivity of cells passing through a cell-interrogation zone in the flow cell. Light scatter from the cells passing through the cell-interrogation zone is measured by the light scatter detection system. The light scatter detection system measures the light scatter parameters of upper median light scatter, lower median angle light scatter, low angle light scatter, and axial light loss. The presented methods for analyzing a blood sample generally include aspirating a whole blood sample into a blood analysis instrument, preparing the blood sample for analysis, passing the blood sample through a flow cell in a transducer system, and measuring axial light loss, multiple angles of light scatter, DC impedance and/or RF conductivity.

19 Claims, 12 Drawing Sheets

TRANSDUCER MODULE

BACKGROUND OF THE INVENTION

1. Field of the Invention

The present invention relates to systems and methods for analyzing a whole blood sample. More specifically, the present invention relates to a transducer module for use in a blood analysis instrument.

2. Background Art

In diagnosing different illnesses and disease states, it is common to analyze a patient's peripheral blood to differentiate and enumerate the various constituents within the blood, as well as to determine certain parameters or characteristics of those constituents. For example, a whole blood sample (WBS) generally comprises various types of cells (both blood cells and non-blood cells) suspended in a liquid medium or plasma. The blood cells are three basic types, namely, red cells (erythrocytes), white cells (leukocytes), and platelets (thrombocytes). Depending on the level of maturity, red cells are often further classified into three subsets, namely, nucleated red blood cells (NRBCs), reticulated red cells ("retics"), and mature red blood cells (RBCs). Mature white cells fall into one of five different subsets, namely, monocytes, lymphocytes, eosinophils, neutrophils and basophils. Each of the white cell subsets can be further classified into subclasses based on their respective level of maturity, activation or abnormality. Platelets are of three general types, namely, mature platelets, reticulated platelets and large platelets. A thorough blood analysis determines the respective concentrations and relative percents of each of the above cell types and subsets.

Various measurement techniques, alone or in combination, have been implemented in blood analysis instruments to differentiate and enumerate the various constituents in a WBS. For example, direct current (DC) impedance measurements are used to measure the volume of a cell. DC impedance measurements accurately size a cell within an isotonic diluent regardless of the cell type, orientation, maturity, and/or other characteristics. Radio frequency (RF) measurements are used to measure the conductivity of a cell to collect information about cell size and internal structure, including chemical composition and nuclear volume. Further, when a cell is irradiated by a light source, such as a laser beam, the cell scatters light in all directions. Measurements of light scatter at various distinct angles are used to obtain information such as cellular granularity, nuclear lobularity, and cell surface structure. Fluorescence measurements of a stained blood sample have been used for differentiating blood sample constituents. The respective outputs of these measurement techniques are then processed to identify and enumerate the constituents and thereby develop a comprehensive blood analysis report.

U.S. Pat. No. 6,228,652 ("the '652 patent"), which is hereby incorporated by reference in its entirety, discloses, inter alia, a blood analysis instrument. The blood analysis instrument of the '652 patent includes a single transducer for simultaneously measuring the DC impedance, RF conductivity, light scattering, and fluorescence characteristics of blood cells passing one-at-a-time through a cell-interrogation zone in a flow cell. A laser is used for irradiating the cells passing through the cell-interrogation zone. The light scatter from the individual cells is then measured. Simultaneously, the fluorescence of each cell is measured to identify NRBC populations. However, the use of fluorescence to identify NRBCs is relatively expensive due to the high costs of the system components and fluorescent dyes needed to stain the blood sample. Further, in practice, the relatively tight tolerances needed for optical focusing and alignment of the laser within the cell-interrogation zone presents a significant manufacturing challenge.

U.S. Pat. No. 7,208,319 ("the '319 patent"), which is hereby incorporated by reference in its entirety, discloses, inter alia, alternative methods for differentiating NRBCs. The methods of the '319 patent include passing a prepared blood sample through a flow cell, irradiating the individual cells of the sample as they pass through the cell-interrogation zone of the flow cell, and measuring combinations of DC impedance, axial light loss, low angle light scatter, and median angle light scatter.

Additional systems and methods are described in U.S. Pat. Nos. 5,125,737; 5,616,501; 5,874,311; 6,232,125; 7,008,792; and 7,208,319, the disclosures of which are hereby incorporated by reference in their entireties.

BRIEF SUMMARY OF THE INVENTION

Provided herein are transducer modules for use in a blood analysis instrument and methods for analyzing a blood sample. The transducer modules presented generally include a light source, a focus-alignment system, a flow cell, and a light scatter detection system. Electrodes within the flow cell allow for the measurement of the DC impedance and RF conductivity of cells passing through a cell-interrogation zone in the flow cell. Light scatter from the cells passing through the cell-interrogation zone is measured by the light scatter detection system. The light scatter detection system measures the light scatter parameters of upper median light scatter, lower median angle light scatter, low angle light scatter, and axial light loss. The presented methods for analyzing a blood sample generally include aspirating a whole blood sample into a blood analysis instrument, preparing the blood sample for analysis, passing the blood sample through a flow cell in a transducer system, and measuring axial light loss, multiple angles of light scatter, DC impedance and/or RF conductivity.

BRIEF DESCRIPTION OF THE FIGURES

The accompanying drawings, which are incorporated herein, form part of the specification and illustrate embodiments of a transducer module and methods for analyzing a blood sample. Together with the description, the drawings further serve to explain the principles of and to enable a person skilled in the relevant art(s) to make and use the transducer modules and methods described herein. In the drawings, like reference numbers indicate identical or functionally similar elements.

DETAILED DESCRIPTION OF EMBODIMENTS

The following detailed description of transducer modules and methods for analyzing a whole blood sample (WBS) refers to the accompanying drawings that illustrate exemplary embodiments. Other embodiments are possible. Modifications may be made to the embodiments described herein without departing from the spirit and scope of the present invention. Therefore, the following detailed description is not meant to be limiting. Further, it would be apparent to one of skill in the art that the systems and methods described below may be implemented in many different embodiments of hardware, software, and/or firmware. Any actual hardware, software, and/or firmware described is not meant to be limiting. The operation and behavior of the systems and methods presented are described with the understanding that modifications and variations of the embodiments are possible given the level of detail presented.

Before describing the presented transducer modules and methods for analyzing a WBS in detail, it is helpful to describe an example environment in which the transducer modules and methods may be implemented. As discussed above, various blood analysis instruments have been developed to differentiate and enumerate various constituents in a WBS. As such, the transducer modules and methods presented herein are particularly useful in the environment of a blood analysis instrument. While the description provided incorporates the transducer modules and methods into a blood analysis instrument, the transducer modules and methods should not be limited to the environment of a blood analysis instrument. One of skill in the art would readily understand how to incorporate the presented transducer modules and methods in alternative environments, such as, for example, flow cytometry systems, cell sorting systems, DNA analysis systems, etc.

Figure 1:
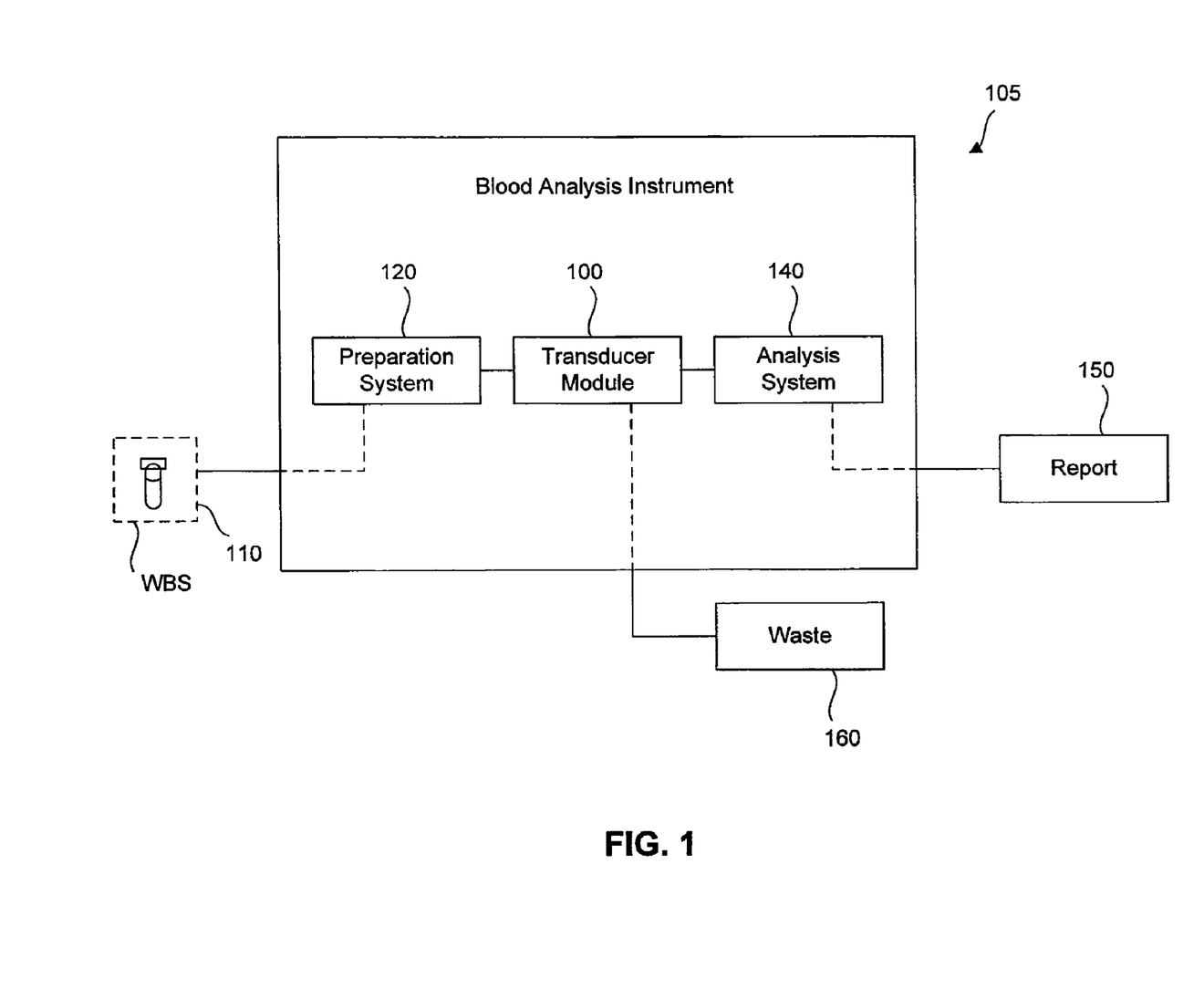
FIG. 1 is a system block diagram of a blood analysis instrument incorporating a transducer module in accordance with one embodiment presented herein.

FIG. 1 is a system block diagram a transducer module 100 incorporated in a blood analysis instrument 105. Within instrument 105 are three core system blocks, namely, a preparation system 120, a transducer system or module 100, and an analysis system 140. While instrument 105 is herein described at a very high level, with reference only to the three core system blocks (120, 100, and 140), one of skill in the art would readily understand that instrument 105 includes many other system components such as central control processor(s), display system(s), fluidic system(s), temperature control system(s), user-safety control system(s), etc.

In operation, a whole blood sample (WBS) 110, is presented to instrument 105 for analysis. WBS 110 is preferably aspirated into instrument 105. Aspiration techniques are known to those skilled in the relevant art. After aspiration, WBS 110 is delivered to preparation system 120. Preparation system 120 receives WBS 110 and performs the operations necessary to prepare WBS 110 for further measurement and analysis. For example, preparation system 120 may separate WBS 110 into predefined aliquots for presentation to transducer module 100. Preparation system 120 may also include mixing chambers so that appropriate reagents may be added to the aliquots. For example, if an aliquot is to be tested for differentiation of white blood cell subset populations, a lysing reagent may be added to the aliquot to break up and remove the RBCs. Preparation system 120 may also include temperature control components to control the temperature of the reagents and/or mixing chambers. Appropriate temperature controls improve the consistency of the operations of preparation system 120.

From preparation system 120, the predefined aliquots are transferred to transducer module 100. As described in further detail below, transducer module 100 performs the intended measurements. The measured parameters are then delivered to analysis system 140 for data processing. Analysis system 140 includes computer processing algorithms to evaluate the measured parameters, identify and enumerate the WBS constituents, and thereafter produce a comprehensive blood analysis report 150. Finally, excess sample from transducer module 100 is directed to an external (or alternatively internal) waste system 160.

Figure 2:
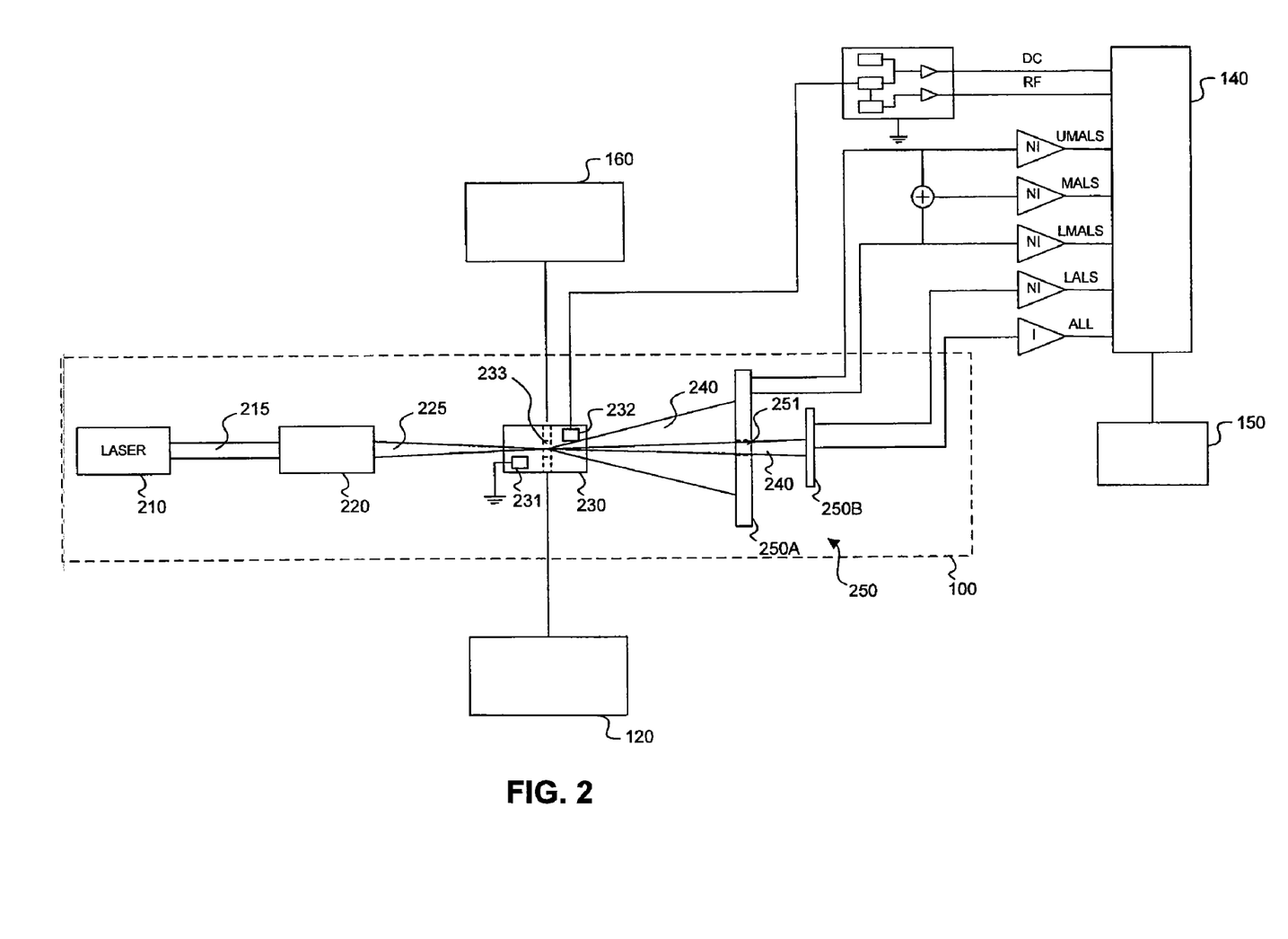
FIG. 2 is a block diagram of the transducer module of FIG. 1.

FIG. 2 is a system block diagram illustrating components of transducer module 100. Transducer module 100 includes a light source, such as a laser 210. In one embodiment, laser 210 is a 635 nm, 5 mW, solid-state laser. Laser 210 emits a beam 215.

In the embodiment shown, a focus-alignment system 220 adjusts beam 215 such that a resulting beam 225 is focused and positioned at a cell-interrogation zone 233 of a flow cell 230. Flow cell 230 receives a sample aliquot from preparation system 120. In one embodiment, additional fluidics (not shown) are employed to allow for hydrodynamic focusing of the sample aliquot within flow cell 230. The aliquot generally flows through the cell-interrogation zone 233 such that its constituents pass through the cell-interrogation zone 233 one at a time. In one embodiment, a cell-interrogation zone, such as the one described in the '652 patent, is employed. For example, cell-interrogation zone 233 may be defined by a square transverse cross-section measuring approximately 50×50 microns, and having a length (measured in the direction of flow) of approximately 65 microns.

As would be appreciated by one of skill in the art, flow cell 230 includes two electrodes 231, 232 for performing DC impedance and RF conductivity measurements of the cells passing through cell-interrogation zone 233. The signals from electrodes 231, 232 are then transmitted to analysis system 140.

Figure 7:
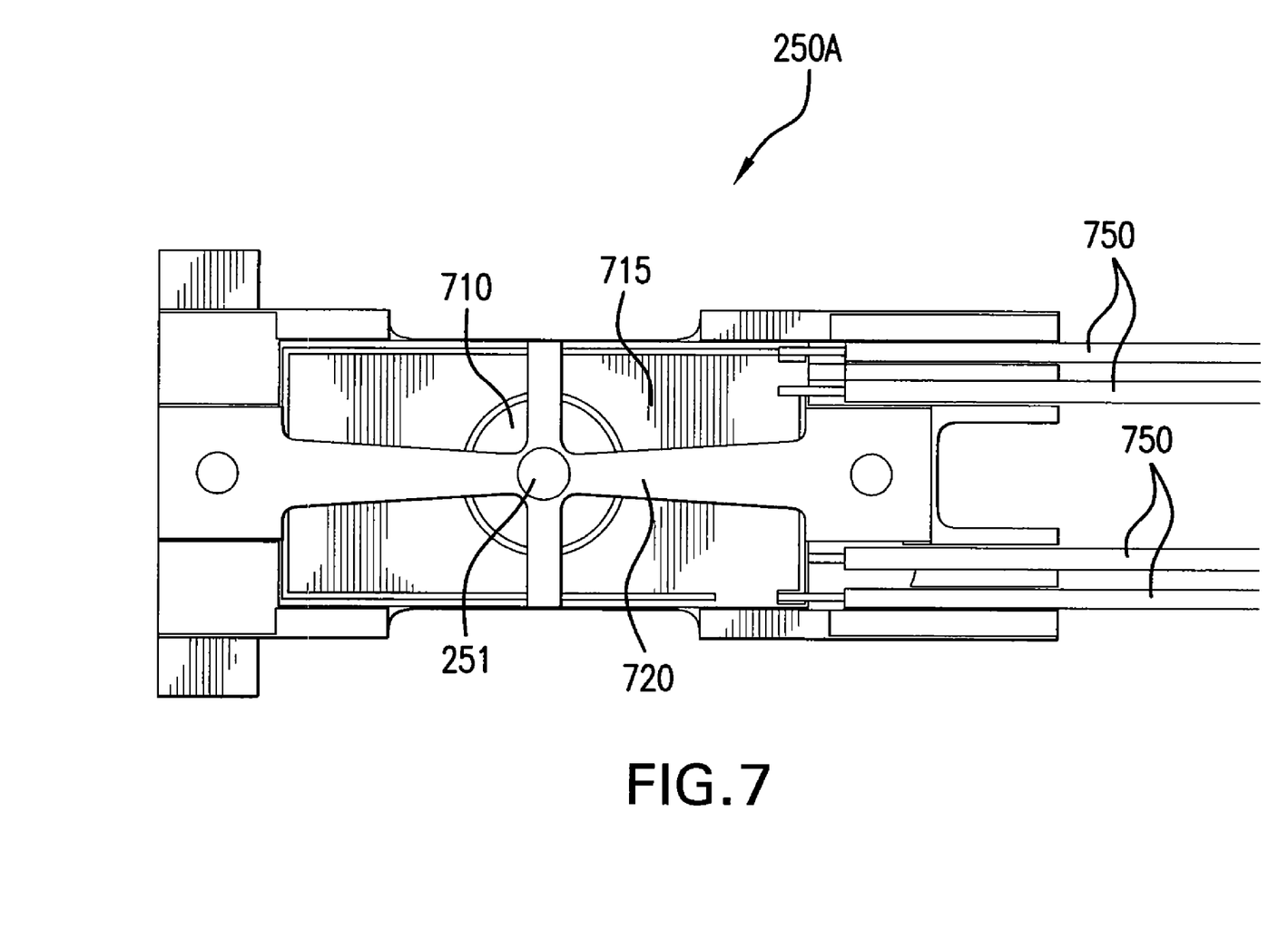
FIG. 7 is a sectional view of a light scatter detector unit in accordance with one embodiment presented herein.

Beam 225 irradiates the cells passing through cell-interrogation zone 233, resulting in light scatter 240. In the embodiment shown in FIG. 2, light scatter 240 is detected by a light scatter detector assembly 250. Light scatter detector assembly 250 differs from previously available assemblies in that it comprises a first light scatter detector unit 250A and a second light scatter detector unit 250B posterior to the first. As best illustrated in FIG. 7, first light scatter detector unit 250A includes a first photoactive region 715 for detecting and measuring upper median angle light scatter (UMALS). First light scatter detector unit 250A also includes a second photoactive region 710 for detecting and measuring lower median angle light scatter (LMALS). In one embodiment, first light scatter detector unit 250A further includes one or more masks to block light scatter in selective portions of the photoactive regions and thereby improve the detector's signal-to-noise ratio. For example, in the embodiment shown in FIG. 7, mask 720 is provided. Further, in the embodiment shown in FIG. 7, an opening 251 is provided to allow low angle light scatter to pass beyond first light scatter detector unit 250A and thereby reach and be detected by second light scatter detector unit 250B. Wires 750 transmit the signal from light scatter detector unit 250A to analysis system 140 for further processing.

Figure 8:
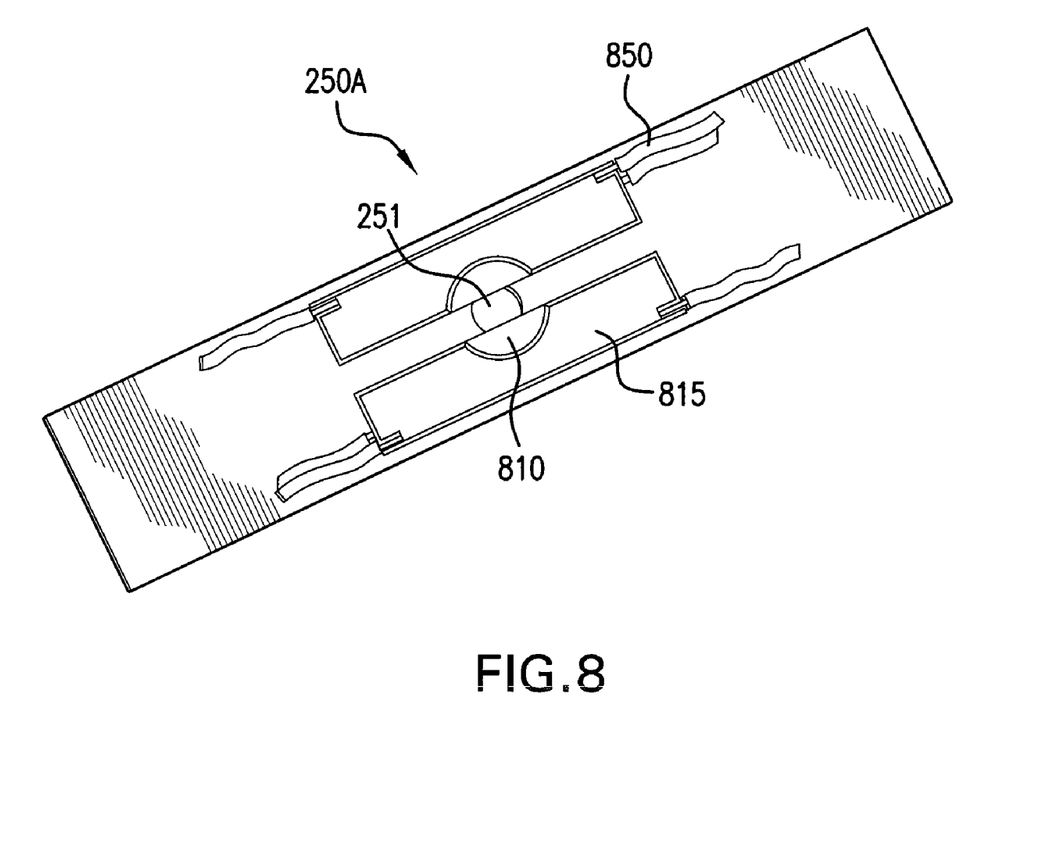
FIG. 8 is a sectional view of a light scatter detector unit in accordance with another embodiment presented herein.

In an alternative embodiment, as shown in FIG. 8, first light scatter detector unit 250A may be designed as a split sensor. As shown in FIG. 8, first light scatter detector unit 250A includes a first photoactive region 815 for detecting and measuring upper median angle light scatter (UMALS), and a second photoactive region 810 for detecting and measuring lower median angle light scatter (LMALS). Opening 251 is provided to allow low angle light scatter to pass beyond first light scatter detector unit 250A and thereby reach and be detected by second light scatter detector unit 250B. While opening 251 is shown as a circular opening in FIGS. 7 and 8, opening 251 is not limited in size or shape, and may be designed in to any appropriate size or shape. Wires 850 transmit the signal from light scatter detector unit 250A to analysis system 140 for further processing.

In one embodiment, a second light scatter detector unit 250B includes one or more low angle light scatter (LALS) sensors. In the embodiment illustrated in FIG. 9, second light scatter detector unit 250B includes four LALS sensors 970 disposed radially around an axial light loss (ALL) sensor 960. LALS sensors 970 and ALL sensor 960 are mounted on a base board 910, such as a printed circuit board (PCB), and covered by a mask 325. In the embodiment shown, a plurality of bolts 930 (only one bolt shown) are used to secure mask 325 to board 910. A plurality of openings 920 in mask 325, including a central opening 921, allows for a more precise control of the light scatter angles that reach the sensors 960, 970. Use of mask 325 allows a manufacturer to limit the light scatter angles beyond the manufacturing limits of the LALS sensors and ALL sensor. For example, a manufacturer can use oversized LALS sensors and then employ mask 325 to define the precise light scatter angles to be measured. If the LALS and ALL sensors are manufactured to the appropriate tolerances, then there would be no need for mask 325.

Figure 9:
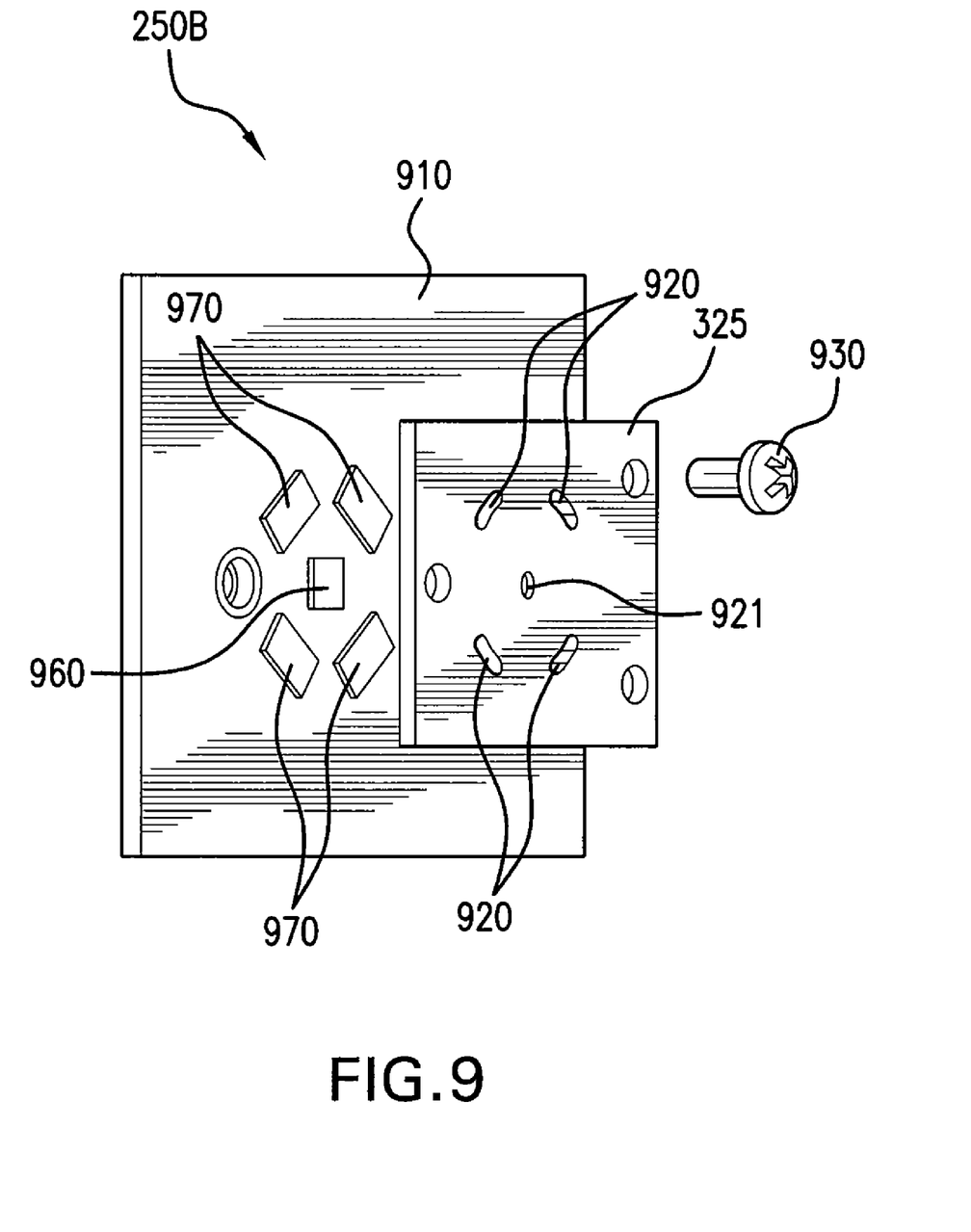
FIG. 9 is a sectional view of a light scatter detector unit in accordance with another embodiment presented herein.

In one embodiment, first photoactive region 815 is used to detect and measure UMALS, which is defined as light scatter at angles between about 20 and about 43 degrees. In alternative embodiments, first light scatter detector unit 250A can be sized and/or positioned such that first photoactive region 815 is used to detect and measure light scatter at angles greater than about 43 degrees. Second photoactive region 810 is used to detect and measure LMALS, which is defined as light scatter at angles between about 9 and about 19 degrees. In alternative embodiments, first light scatter detector unit 250A can be sized and/or positioned such that second photoactive region 815 is used to detect and measure light scatter at angles less than about 9 degrees. A combination of UMALS and LMALS is defined as median angle light scatter (MALS), which is light scatter at angles between about 9 degrees and about 43 degrees. LALS sensors 970 are used to detect and measure LALS, which is defined as light scatter at angles less than about 10 degrees, including 1.9 degrees ±0.5 degrees, 3.0 degrees ±0.5 degrees, 3.7 degrees ±0.5 degrees, 5.1 degrees ±0.5 degrees, 6.0 degrees ±0.5 degrees, and 7.0 degrees ±0.5 degrees. ALL sensor 960 is used to detect and measure light loss at angles less than about one degree, and in one embodiment angles less than about 0.5 degrees. As such, the assembly presented, and equivalent structures, differ from previously available assemblies in that they provide means for detecting and measuring ALL and multiple distinct light scatter angles. For example, light scatter detector assembly 250, including appropriate circuitry and/or processing units, provide a means for detecting and measuring UMALS, LMALS, LALS, MALS and ALL.

Figure 3:
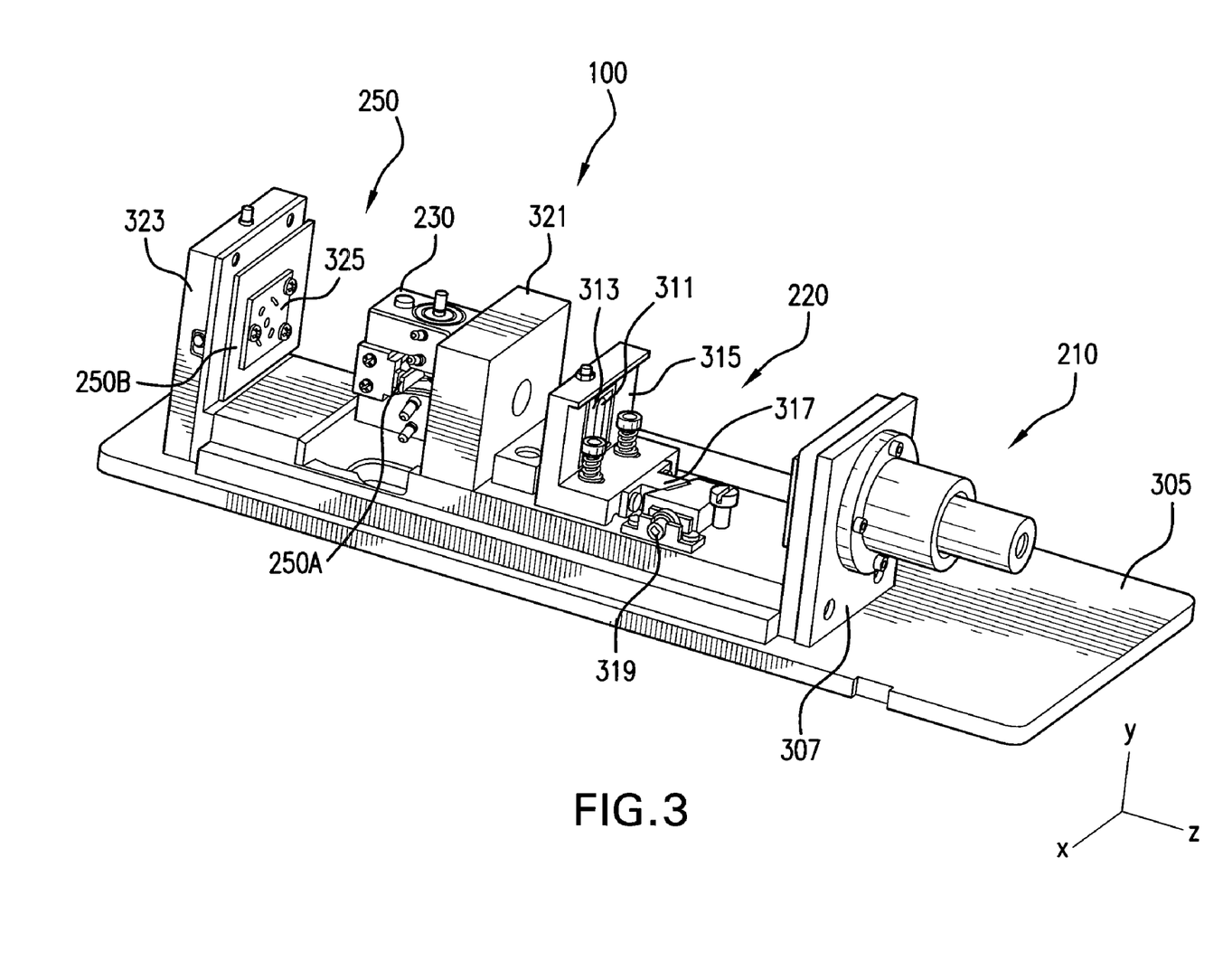
FIG. 3 is a perspective view of a transducer module in accordance with one embodiment presented herein.
Figure 4:
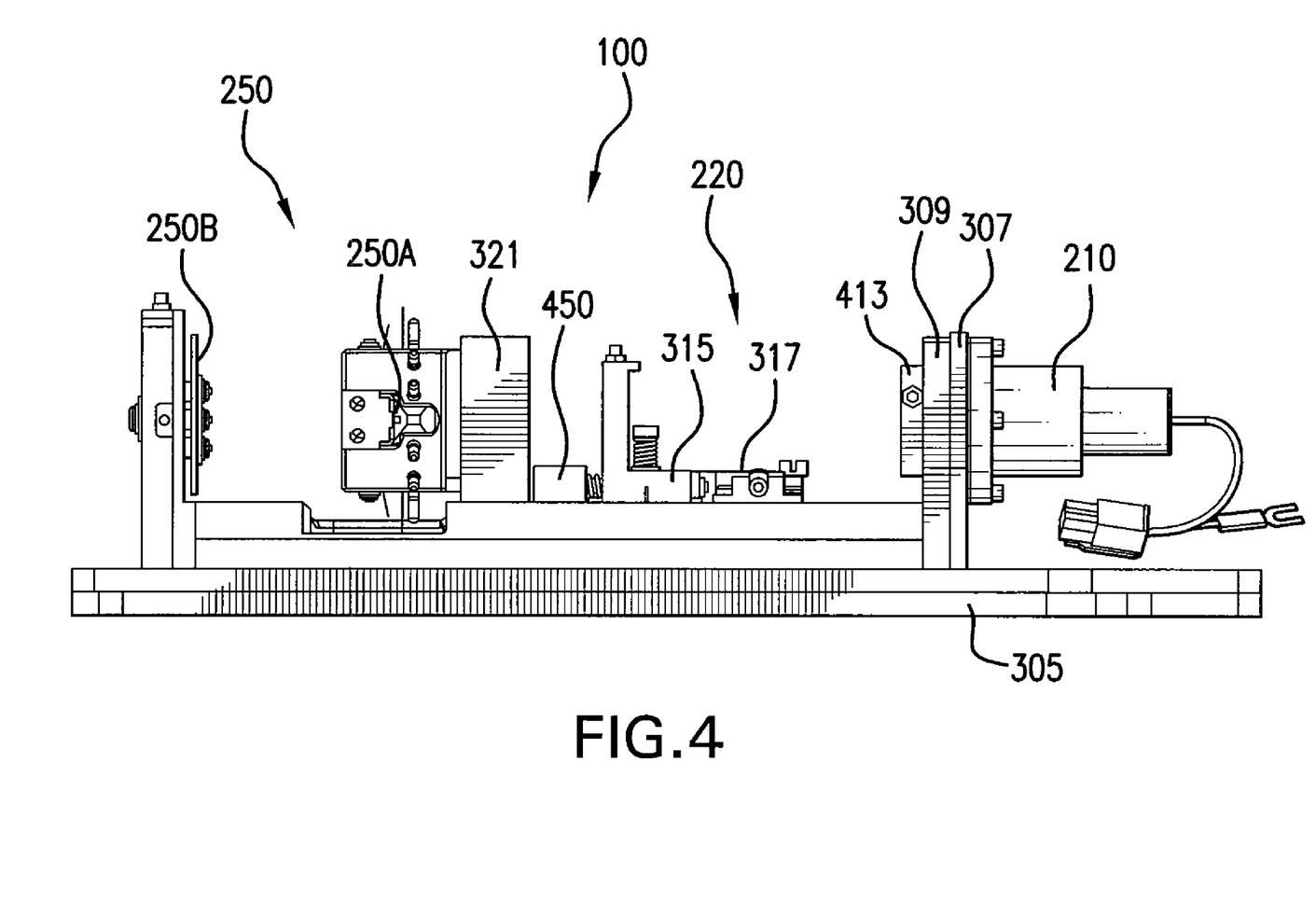
FIG. 4 is a side view of the transducer module of FIG. 3.
Figure 5:
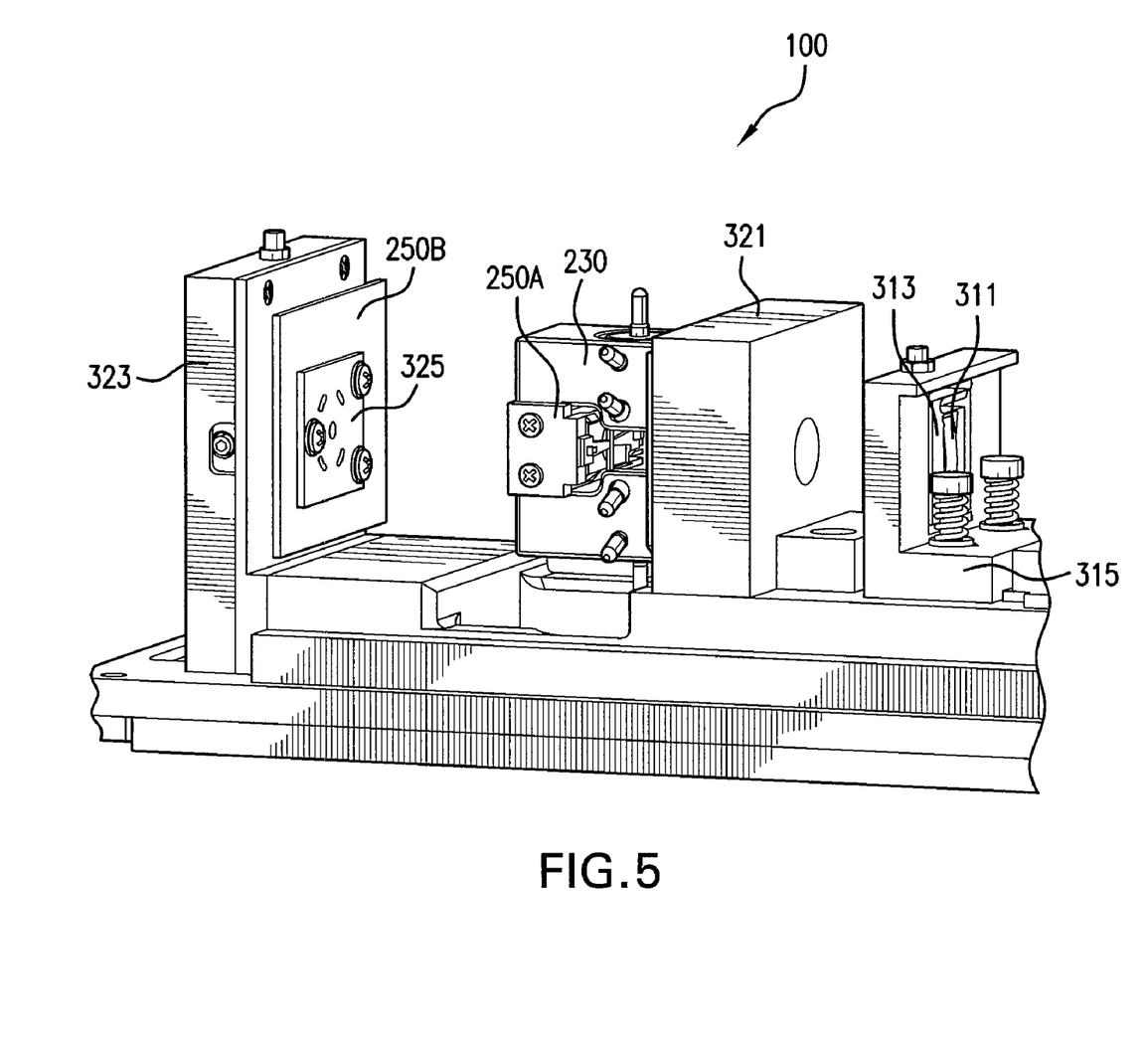
FIG. 5 is a sectional view of the transducer module of FIG. 3.
Figure 6:
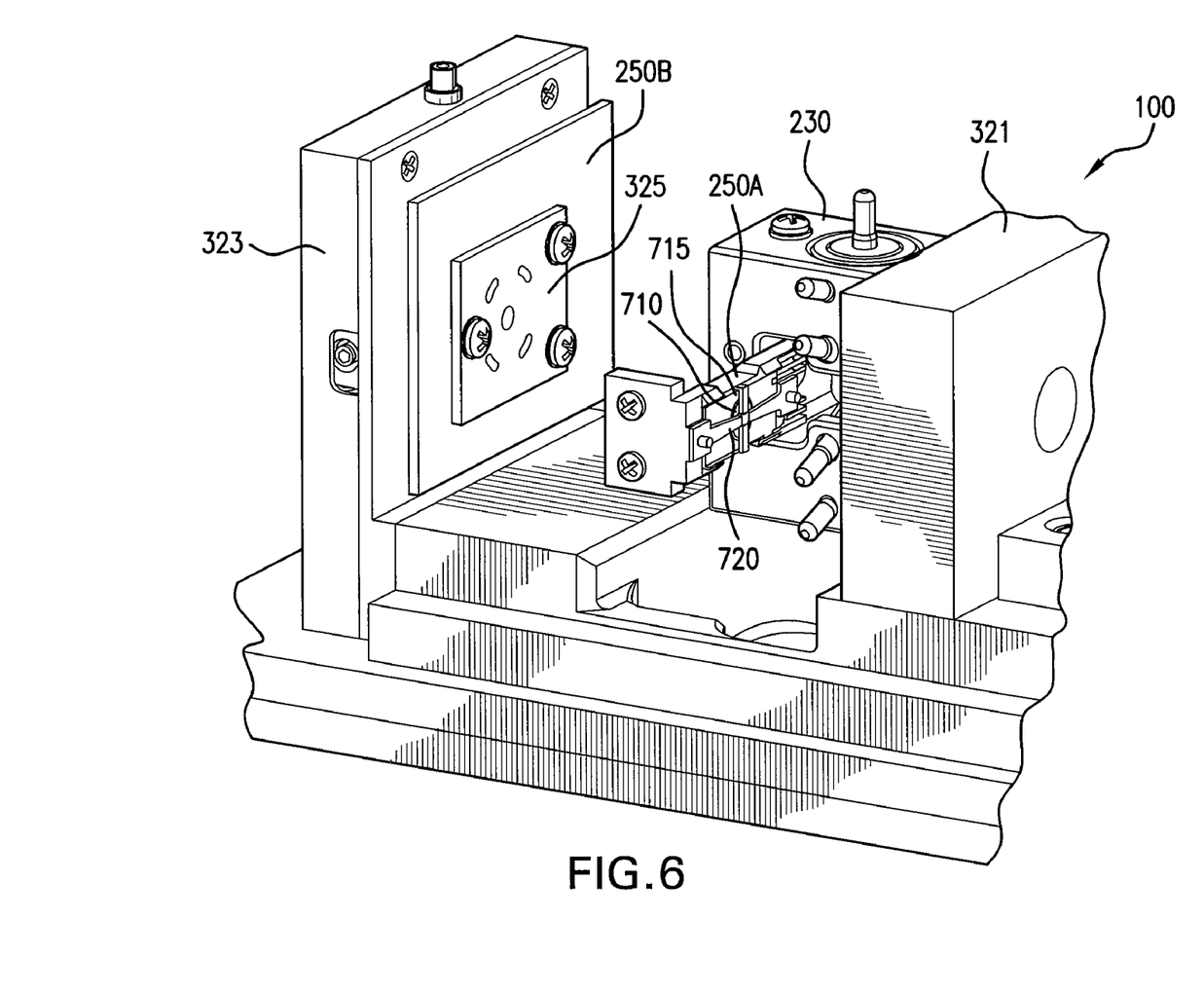
FIG. 6 is an alternative sectional view of the transducer module of FIG. 3.

FIG. 3 is a perspective view of a transducer module 100 in accordance with one embodiment presented herein. FIG. 4 is a side view of the transducer module of FIG. 3. FIG. 5 is a blown-up sectional view of transducer module 100 showing first light scatter detector unit 250A appropriately mounted within flow cell 230. FIG. 6 is an alternative sectional view of transducer module 100. For illustrative purposes, FIG. 6 depicts first light scatter detector unit 250A partially withdrawn from flow cell 230.

In the embodiment depicted in FIGS. 3-6, transducer module 100 generally includes a relatively fixed laser 210, focus-alignment system 220, a relatively fixed flow cell 230, and light scatter detector assembly 250. These components are mounted on a base board 305, and thereafter incorporated into a blood analysis instrument. One of skill in the art would readily understand that in alternative embodiments one or more components of transducer module 100 may be removed or repositioned. One of skill in the art would also readily understand that in alternative embodiment one or more components of transducer module 100 may be replaced with equivalent components to perform similar functions.

Figure 10:
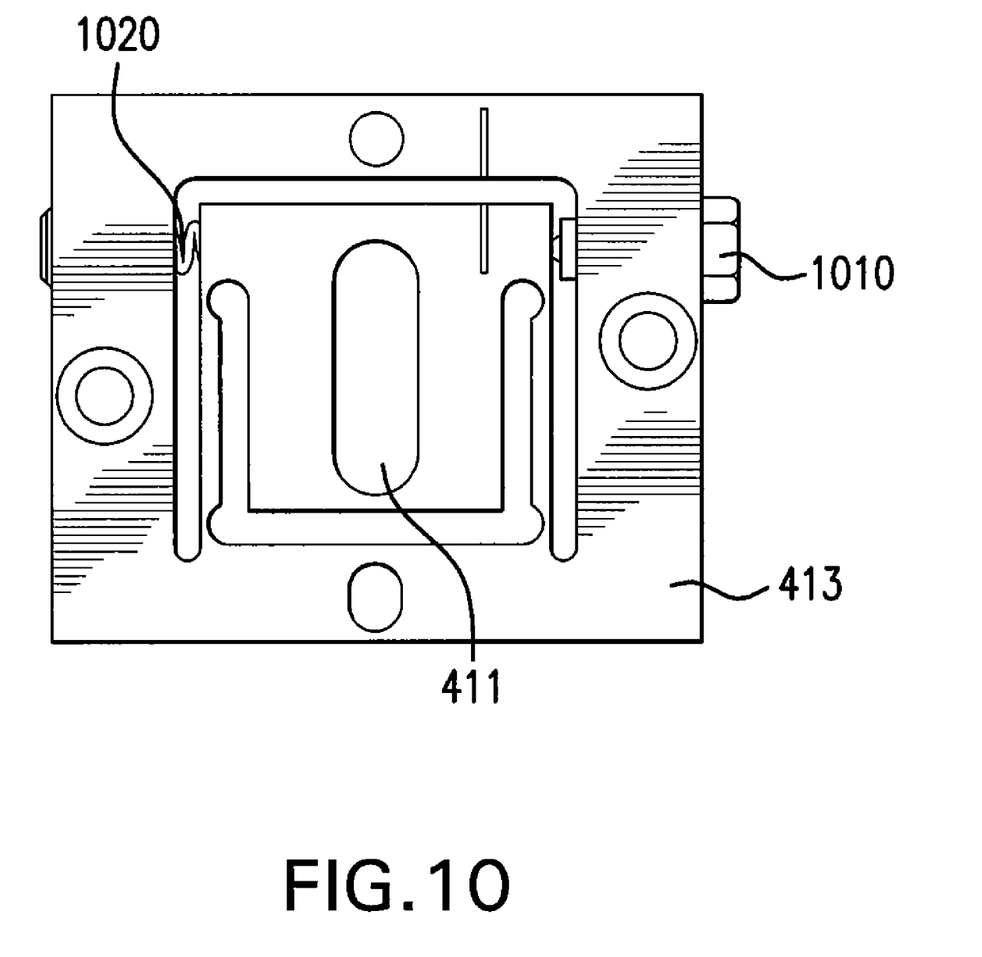
FIG. 10 is a sectional view of a lens mounted on a flexure hinge in accordance with one embodiment presented herein.
Figure 11:
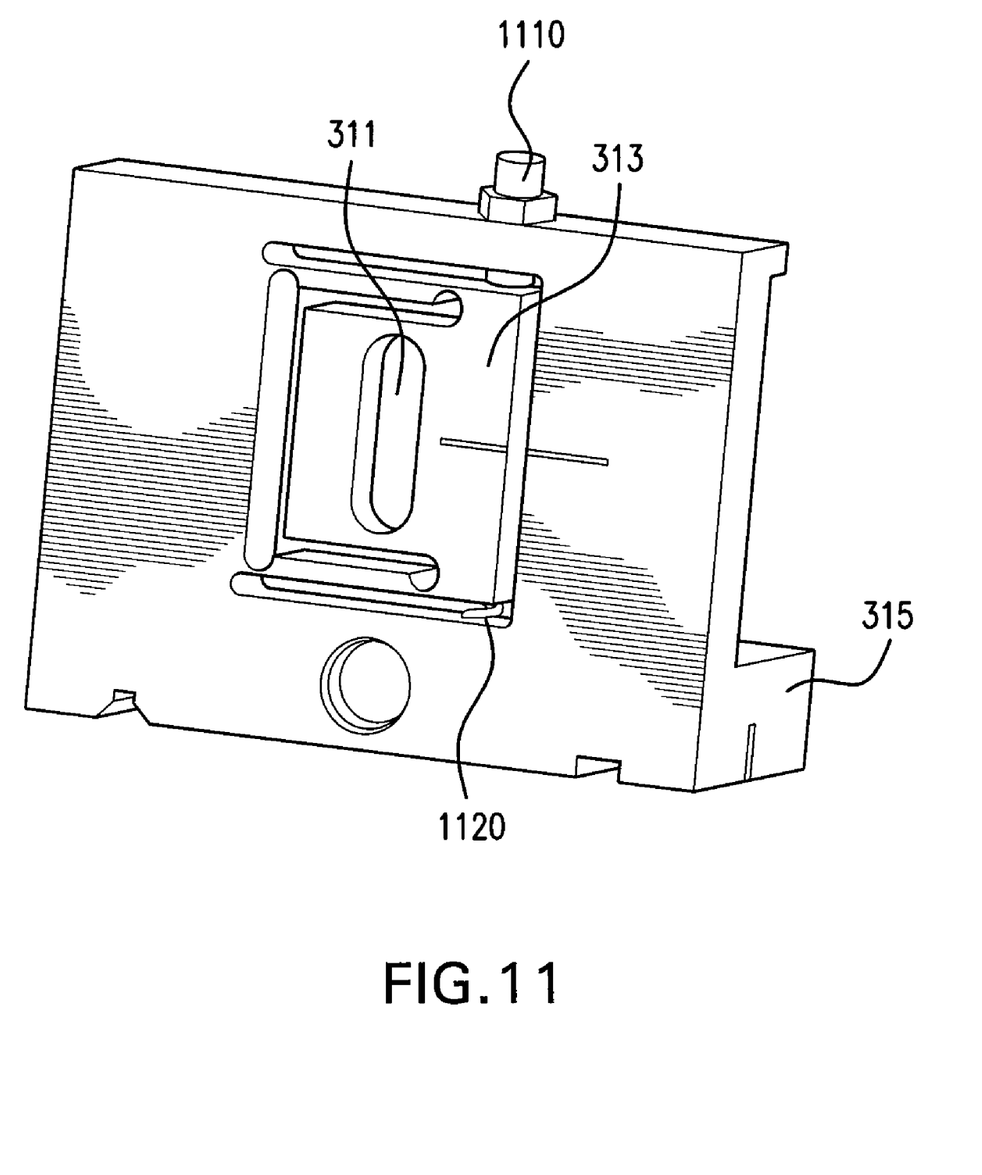
FIG. 11 is a sectional view of a lens mounted on a flexure hinge in accordance with one embodiment presented herein.

In the embodiment shown, laser 210 is mounted on block 307 in a relatively fixed position. As used herein, the term "fixed" or "relatively fixed" is not intended to mean permanently set, but instead is intended to mean "anchored such that an end-user does not need to make positional adjustments." The relatively fixed position of laser 210 contrasts with previously available systems where an end-user would have to conduct tedious and time-consuming adjustments of both the laser and flow cell in order to properly focus and position the laser beam in the cell-interrogation zone of the flow cell. In the system depicted in FIGS. 3 and 4, the beam emitted by laser 210 is focused and positioned by focus-alignment system 220. Focus-alignment system 220 includes a first lens 411 mounted on a first adjustment means 413 (as best shown in FIG. 10) and a second lens 311 mounted on a second adjustment means 313 (as best shown in FIG. 11), wherein the second adjustment means is mounted on a movable carrier 315.

In the embodiment shown, first adjustment means 413 is a flexure hinge, mounted on block 309. As depicted, first adjustment means 413 includes a set screw 1010 and an adjustment spring 1020 for positional adjustment of first lens 411. The positional adjustment of first lens 411 thereby provides lateral movement, and thus lateral alignment, of the laser beam passing through first lens 411. Flexure hinges are well known, as described in U.S. Pat. No. 4,559,717, which is hereby incorporated by reference in its entirety. As would be evident to one of skill in the art, any equivalent structure may be employed with the end objective of providing lateral alignment of the laser beam passing through first lens 411. As such, first adjustment means 413, and equivalents thereof, provides means for lateral alignment of the laser beam in the x-direction relative to laser 210.

In the embodiment shown, second adjustment means 313 is a flexure hinge mounted on movable carrier 315. Second adjustment means 313 includes a set screw 1110 and an adjustment spring 1120 for positional adjustment of second lens 311. The positional adjustment of second lens 311 thereby provides longitudinal (or vertical) movement, and thus longitudinal alignment, of the laser beam passing through second lens 311. As would be evident to one of skill in the art, any equivalent structure may be employed with the end objective of providing longitudinal alignment of the laser beam passing through second lens 311. As such, second adjustment means 313, and equivalents thereof, provides means for longitudinal alignment of the laser beam in the y-direction relative to laser 210.

One of skill in the art would understand that although the above described embodiment presents first adjustment means 413 as providing lateral alignment and second adjustment means 313 providing longitudinal alignment, a system wherein first adjustment means 413 provides longitudinal alignment and second adjustment means 313 provides lateral alignment, would be an equivalent system.

Movable carrier 315 is provided to axially position the focal point of the laser beam passing through second lens 311. Movable carrier 315 includes a wedge assembly 317, a biasing spring 450, and a set screw 319 to move movable carrier 315 forward or backward, along the z-direction relative to laser 210. Forward and backward movement of movable carrier 315 places the focal point of the laser beam in cell-interrogation zone 233 of flow 230. As such, movable carrier 315, and equivalents thereof, provides means for axial positioning of the focal point of the laser beam in the z-direction relative to laser 210.

The positional movement and/or adjustment of first adjustment means 413, second adjustment means 313, and movable carrier 315 allows for the precise positioning of the focal point of the laser beam within the cell-interrogation zone 233. As such, a manufacturer may fix flow cell 230 to a system block 321 relative to laser 210, within manufacturable tolerances, and thereafter provide for fine adjustments of the position of the focal point of the laser beam to properly irradiate cell-interrogation zone 233 of flow cell 230.

Upon irradiation by the laser beam, light scatter is detected by a light scatter detector assembly, such as the exemplary light scatter detector assembly 250 described above. For example, light scatter detector assembly 250 is depicted as comprising first light scatter detector unit 250A mounted within flow cell 230 and second light scatter detector unit 250B mounted on system block 323.

Figure 12:
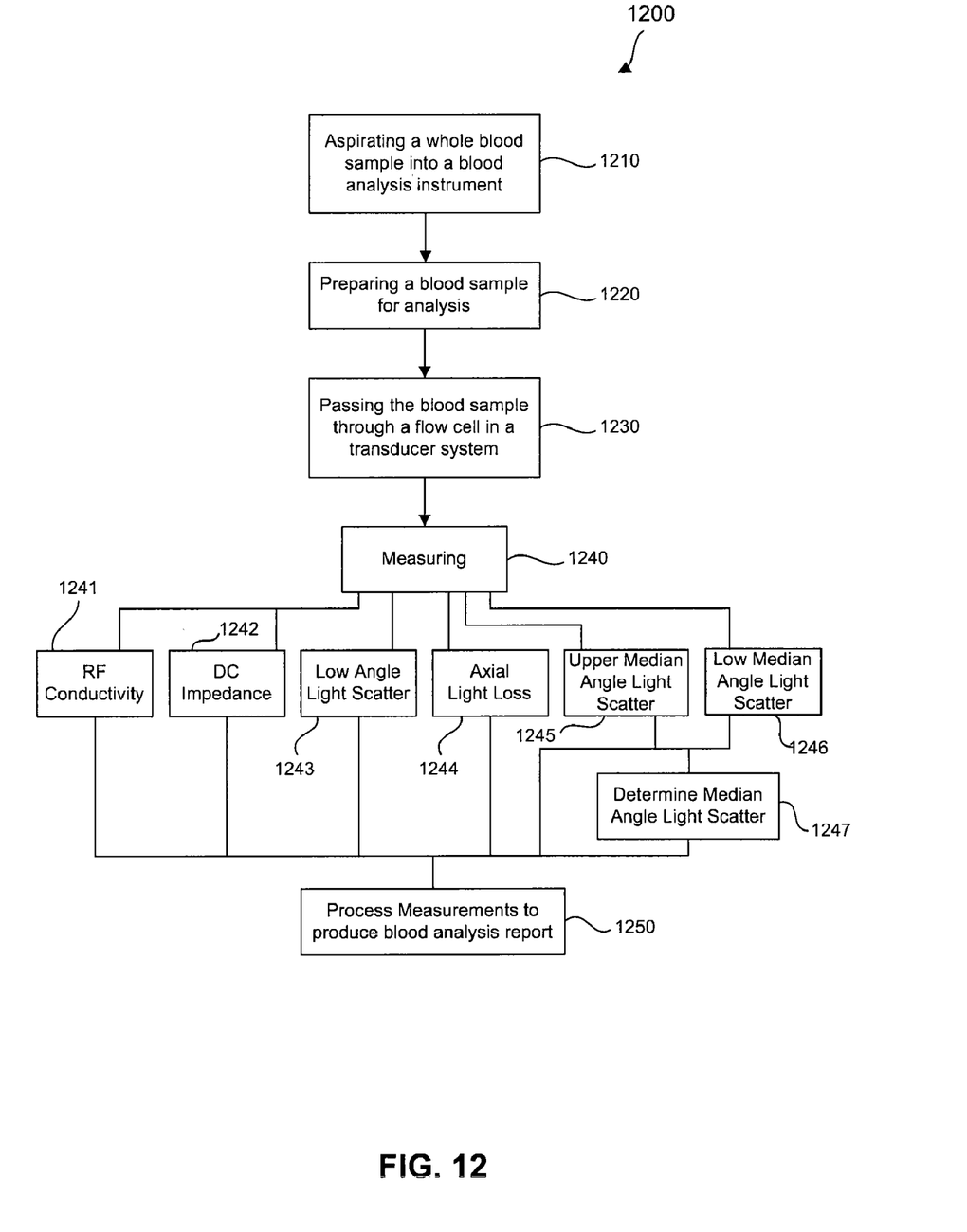
FIG. 12 is a flowchart illustrating a method of analyzing a blood sample.

FIG. 12 is a flowchart illustrating a method 1200 of analyzing a blood sample using, for example, transducer module 100. One of skill in the art would appreciate that the method presented in FIG. 12 is not limited to use solely with the transducer module 100 described herein, but instead can be performed using alternative systems.

In step 1210, a WBS is aspirated into a blood analysis instrument. In step 1220, the blood sample is prepared by dividing the sample into aliquots and mixing the aliquot samples with appropriate reagents. In step 1230, the aliquot samples are passed through a flow cell in a transducer system such that constituents of the aliquot samples pass through a cell-interrogation zone in a one-by-one fashion. The constituents are irradiated by a light source, such as a laser. In step 1240, any combination of RF conductivity 1241, DC impedance 1242, LALS 1243, ALL 1244, UMALS 1245, and/or LMALS 1246 are measured. The measurements of UMALS 1245 and LMALS 1246 may then be used to determine MALS 1247. Alternatively, MALS 1247 may be measured directly. The resulting measurements are then processed, in step 1250, to ultimately produce a blood analysis report. Method 1200 differs from previously known methods in that the system described above allows for the simultaneous measurement of ALL with multiple distinct light scatter angles. For example, method 1200 simultaneously measures UMALS, LMALS, MALS, LALS, and ALL.

EXAMPLES

The following paragraphs serve as examples of the above-described systems. The examples provided are prophetic examples, unless explicitly stated otherwise.

Example 1

In one embodiment, there is provided a light scatter detector assembly comprising a first light scatter detector unit and a second light scatter detector unit. The first light scatter detector unit includes a first photoactive region for detecting UMALS, a second photoactive region for detecting LMALS, and an opening provided to allow low angle light scatter to pass beyond the first light scatter detector unit. The second light scatter detector unit is posterior to the first light scatter detector unit, and includes an axial light loss sensor. The second light scatter detector unit further includes one or more LALS sensors disposed proximate to the axial light loss sensor.

Example 2

In one embodiment, there is provided a laser light focus-alignment system for use in a transducer module, comprising a first adjustment means for lateral alignment of a laser beam and a second adjustment means for longitudinal alignment of the laser beam. The second adjustment means is mounted on a movable carrier such that movement of the carrier axially positions a focal point of the laser beam. In one embodiment, the first adjustment means includes a first lens, wherein positional movement of the first lens aligns the laser beam in a x-direction, the second adjustment means includes a second lens, wherein positional movement of the second lens aligns the laser beam in a y-direction, and the movement of the movable carrier positions the focal point of the laser beam in a z-direction, wherein the x-direction, y-direction, and z-direction are relative to a laser light source. In alternative embodiments, the first adjustment means includes a flexure hinge and the second adjustment means includes a flexure hinge.

Example 3

In one embodiment, there is provide a transducer module comprising a fixed laser light source, a first lens proximate to the laser light source for lateral alignment of a laser beam emitted by the laser light source, a second lens mounted on a movable carrier, wherein the second lens provides longitudinal alignment of the laser beam, and wherein movement of the carrier axially positions a focal point of the laser beam, and a fixed flow cell.

Example 4

In one embodiment, there is provided a transducer module comprising a fixed laser light source, a first lens proximate to the laser light source for lateral adjustment of a laser beam emitted by the laser light source, a second lens mounted on a movable carrier, wherein the second lens longitudinally adjusts the laser beam, and wherein movement of the carrier axially positions a focal point of the laser beam, a fixed flow cell, and a light scatter detector assembly. The light scatter detector assembly includes a first light scatter detector unit having a first photoactive region for detecting UMALS, a second photoactive region for detecting LMALS, and an opening provided to allow low angle light scatter to pass beyond the first light scatter detector unit. The light scatter detector assembly also includes a second light scatter detector unit posterior to the first light scatter detector unit. The second light scatter detector unit includes an ALL sensor. In one embodiment, the transducer module further comprises one or more LALS sensors disposed proximate to the axial light loss sensor.

Example 5

In one embodiment, there is provided a method comprising aspirating a blood sample, preparing the blood sample for analysis, and passing the blood sample through a flow cell in a transducer system such that the transducer system irradiates the blood sample. The method further includes detecting and measuring light scatter parameters of ALL, LALS, UMALS, and LMALS. The method may further comprise detecting and measuring DC impedance, RF conductivity, and MALS. Alternatively, the method may comprise calculating MALS from the measured UMALS and LMALS.

Example 6

In one embodiment, there is provided a method comprising aspirating a blood sample, preparing the blood sample for analysis, and passing the blood sample through a flow cell in a transducer system such that the transducer system irradiates the blood sample, and detecting and measuring ALL and four distinct angles of light scatter.

The foregoing description of the invention has been presented for purposes of illustration and description. It is not intended to be exhaustive or to limit the invention to the precise form disclosed. Other modifications and variations may be possible in light of the above teachings. The embodiments were chosen and described in order to best explain the principles of the invention and its practical application and to thereby enable others skilled in the art to best utilize the invention in various embodiments and various modifications as are suited to the particular use contemplated. It is intended that the appended claims be construed to include other alternative embodiments of the invention.

What is claimed is:

1. A transducer module, comprising:
a relatively fixed laser light source;
a first lens proximate to the laser light source mounted on a flexure hinge configured to only adjust lateral alignment of a laser beam emitted by the laser light source;
a second lens, for longitudinal alignment of the laser beam, wherein the second lens is mounted on a movable carrier and movement of the movable carrier axially positions a focal point of the laser beam; and
a relatively fixed flow cell.

2. A transducer module, comprising:
a relatively fixed laser light source;
a first lens proximate to the laser light source for lateral alignment of a laser beam emitted by the laser light source;
a second lens, for longitudinal alignment of the laser beam, wherein the second lens is mounted on a movable carrier and movement of the movable carrier axially positions a focal point of the laser beam;
a relatively fixed flow cell; and
a light scatter detector assembly including,
a first light scatter detector unit having a first photoactive region for detecting upper median angle light scatter, a second photoactive region for detecting lower median angle light scatter, and an opening provided to allow low angle light scatter to pass beyond the first light scatter detector unit, and
a second light scatter detector unit posterior to the first light scatter detector unit, wherein the second light scatter detector unit includes an axial light loss sensor.

3. The transducer module of claim 2, further comprising:
one low angle light scatter sensor disposed proximate to the axial light loss sensor.

4. The transducer module of claim 2, further comprising:
a plurality of low angle light scatter sensors disposed proximate to the axial light loss sensor.

5. The transducer module of claim 4, wherein the plurality of low angle light scatter sensors are positioned to detect light scatter of about five degrees.

6. The transducer module of claim 2, wherein the first light scatter detector unit includes a mask.

7. The transducer module of claim 2, wherein the second list scatter detector unit includes a mask.

8. The transducer module of claim 2, wherein the first photoactive region detects light scatter at angles greater than about 43 degrees.

9. The transducer module of claim 2, wherein the second photoactive region detects light scatter at angles less than about 9 degrees.

10. The transducer of claim 1, further comprising:
a block; and
a base board,
wherein the laser is mounted on the block, and
wherein the block is mounted on the base board.

11. The transducer of claim 1, further comprising:
a set screw; and
an adjustment spring,
wherein rotation of the set screw adjusts the lateral position of the first lens.

12. The transducer of claim 1, further comprising:
a set screw; and
an adjustment spring,
wherein rotation of the set screw adjusts the position of the second lens.

13. The transducer of claim 1, wherein the movable carrier is configured to move in an axial direction of the transducer module.

14. The transducer of claim 1, wherein the movable carrier comprises:
a set screw, wherein rotation of the set screw adjusts the axial position of the movable carrier.

15. The transducer of claim 1, wherein the first lens, second lens, and flow cell are arranged such that during operation, laser light passes through the first lens and the second lens before passing through the flow cell.

16. The transducer of claim 1, further comprising a relatively fixed base, wherein the laser light source is mounted to the base.

17. The transducer of claim 1, wherein the first lens is configured to adjust in a lateral direction.

18. The transducer of claim 1, wherein the second lens is configured to adjust in a vertical direction.

19. The transducer of claim 16, further comprising:
a wedge assembly comprising:
a first wedge piece adjustably mounted on the base; and
a second wedge piece fixed to the movable carrier,
wherein lateral movement of the first wedge piece adjusts the axial position of the second wedge piece and movable carrier.

* * * * *